(12) United States Patent
McMillan et al.

(10) Patent No.: US 9,086,353 B2
(45) Date of Patent: Jul. 21, 2015

(54) OPTICAL INSTRUMENTS

(76) Inventors: Norman McMillan, Craiguecullen (IE); Martina O'Neill, Dublin (IE); Kevin Arthure, Kildalkey (IE); Stuart Smith, Blessington (IE)

( * ) Notice: Subject to any disclaimer, the term of this patent is extended or adjusted under 35 U.S.C. 154(b) by 47 days.

(21) Appl. No.: 14/111,306

(22) PCT Filed: Apr. 13, 2012

(86) PCT No.: PCT/EP2012/056835
§ 371 (c)(1),
(2), (4) Date: Nov. 20, 2013

(87) PCT Pub. No.: WO2012/140232
PCT Pub. Date: Oct. 18, 2012

(65) Prior Publication Data
US 2014/0085628 A1 Mar. 27, 2014

(30) Foreign Application Priority Data
Apr. 13, 2011 (EP) .................................. 11162343

(51) Int. Cl.
G01N 21/01 (2006.01)
G01N 21/03 (2006.01)

(52) U.S. Cl.
CPC .............. *G01N 21/01* (2013.01); *G01N 21/03* (2013.01)

(58) Field of Classification Search
USPC ................. 356/244, 246, 432–440, 335–343; 422/99, 100, 102, 104; 435/6
See application file for complete search history.

(56) References Cited

U.S. PATENT DOCUMENTS

| | | | |
|---|---|---|---|
| 7,396,509 B2* | 7/2008 | Burns | 422/65 |
| 7,964,413 B2* | 6/2011 | Macioszek et al. | 436/165 |
| 2009/0073435 A1* | 3/2009 | Tsukuda | 356/319 |
| 2010/0045980 A1* | 2/2010 | Tsukuda | 356/319 |

* cited by examiner

*Primary Examiner* — Hoa Pham
(74) *Attorney, Agent, or Firm* — Wood, Phillips, Katz, Clark & Mortimer

(57) ABSTRACT

An optical instrument (10) has a drop-supporting surface for receiving a droplet (98) of liquid with a cover (16) mounted on the housing (12) which receives a light source and provides communication between the light source (114) and the inner surface of the cover. A loading aperture (24) extending through the cover permits access to the drophead when the cover is in a first rotational loading position, and the cover may be rotated to a measurement position in which the light source is positioned to illuminate the drop-supporting surface. A positioning mechanism provided between the cover an the housing engages the cover when it reaches the measurement position and thereby ensures that the light source and drop-supporting surface are maintained in fixed spaced-apart relationship.

14 Claims, 16 Drawing Sheets

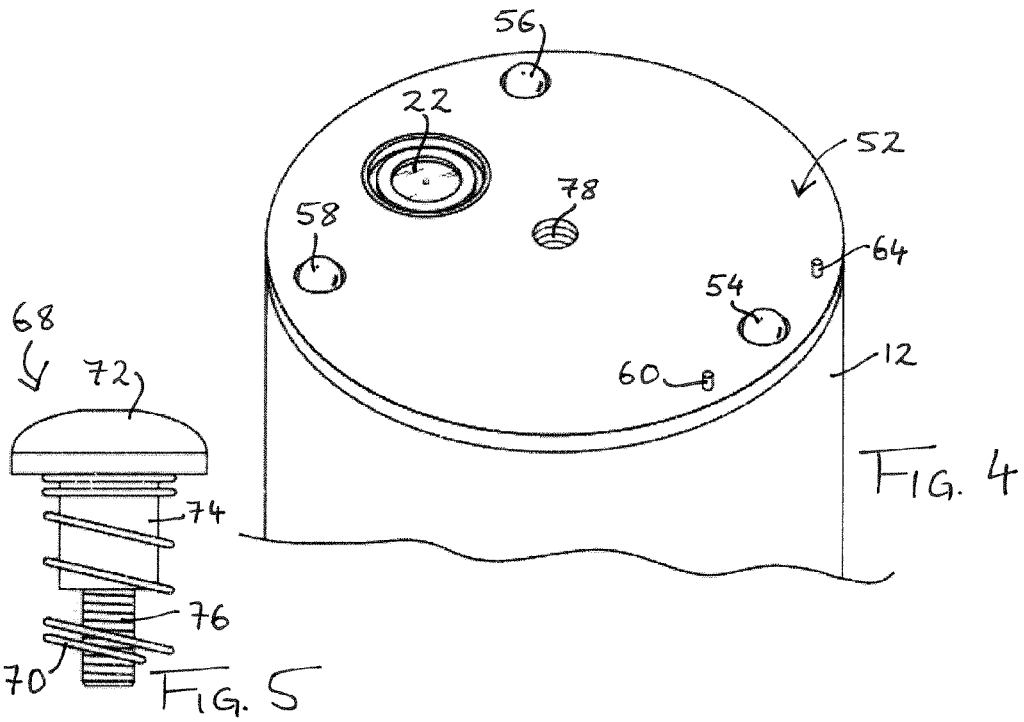
FIG. 4
FIG. 5
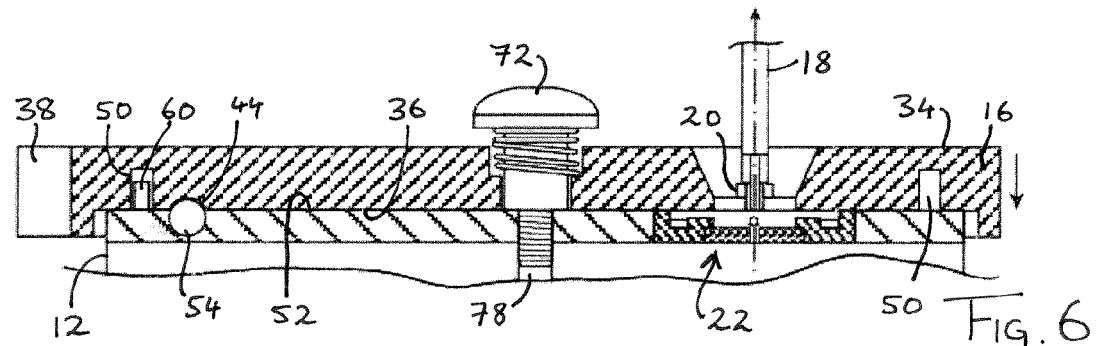
FIG. 6
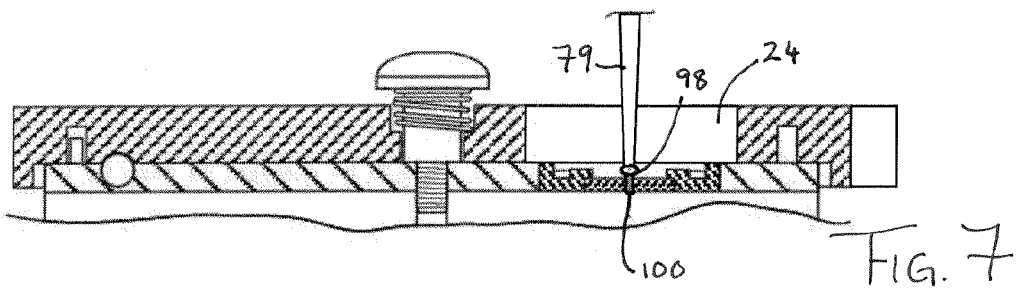
FIG. 7

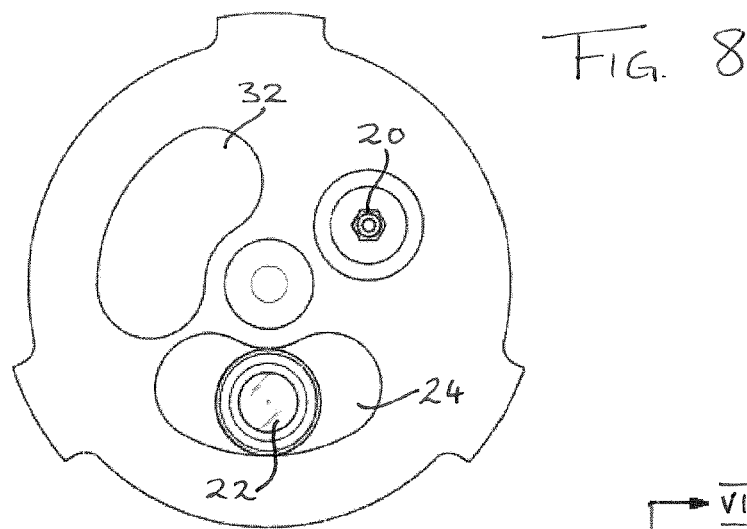
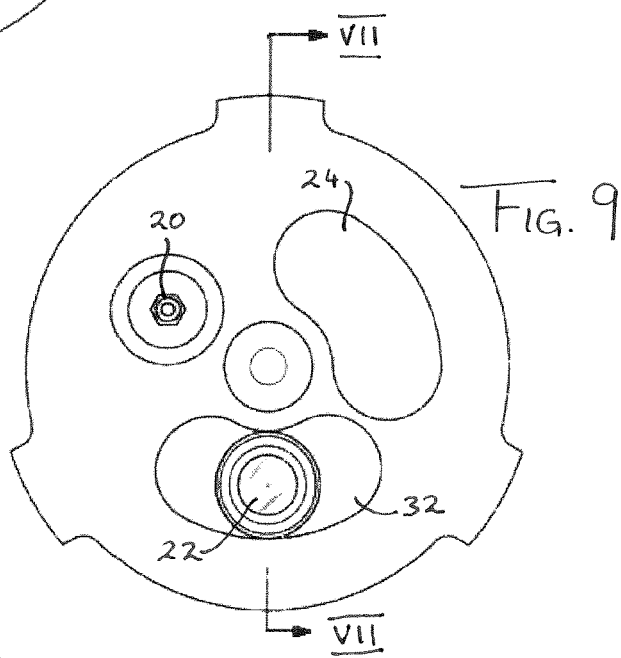
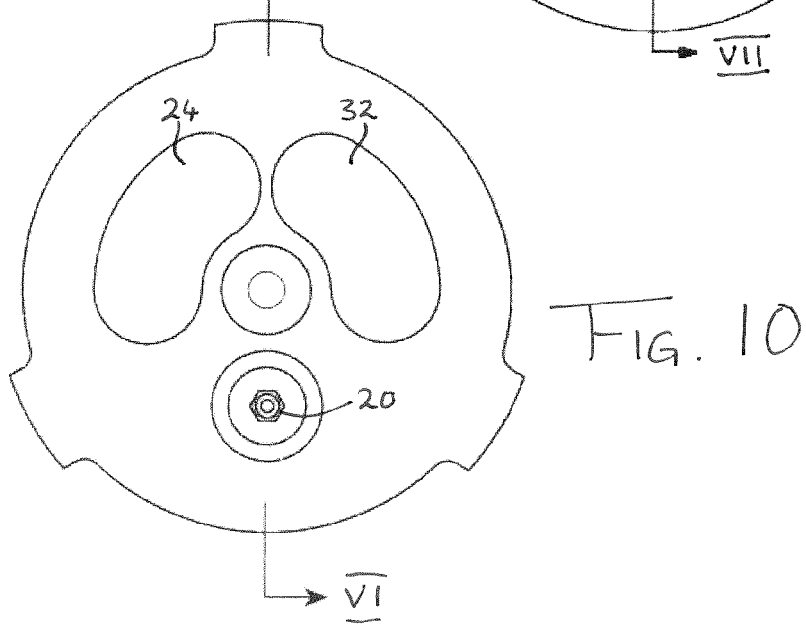

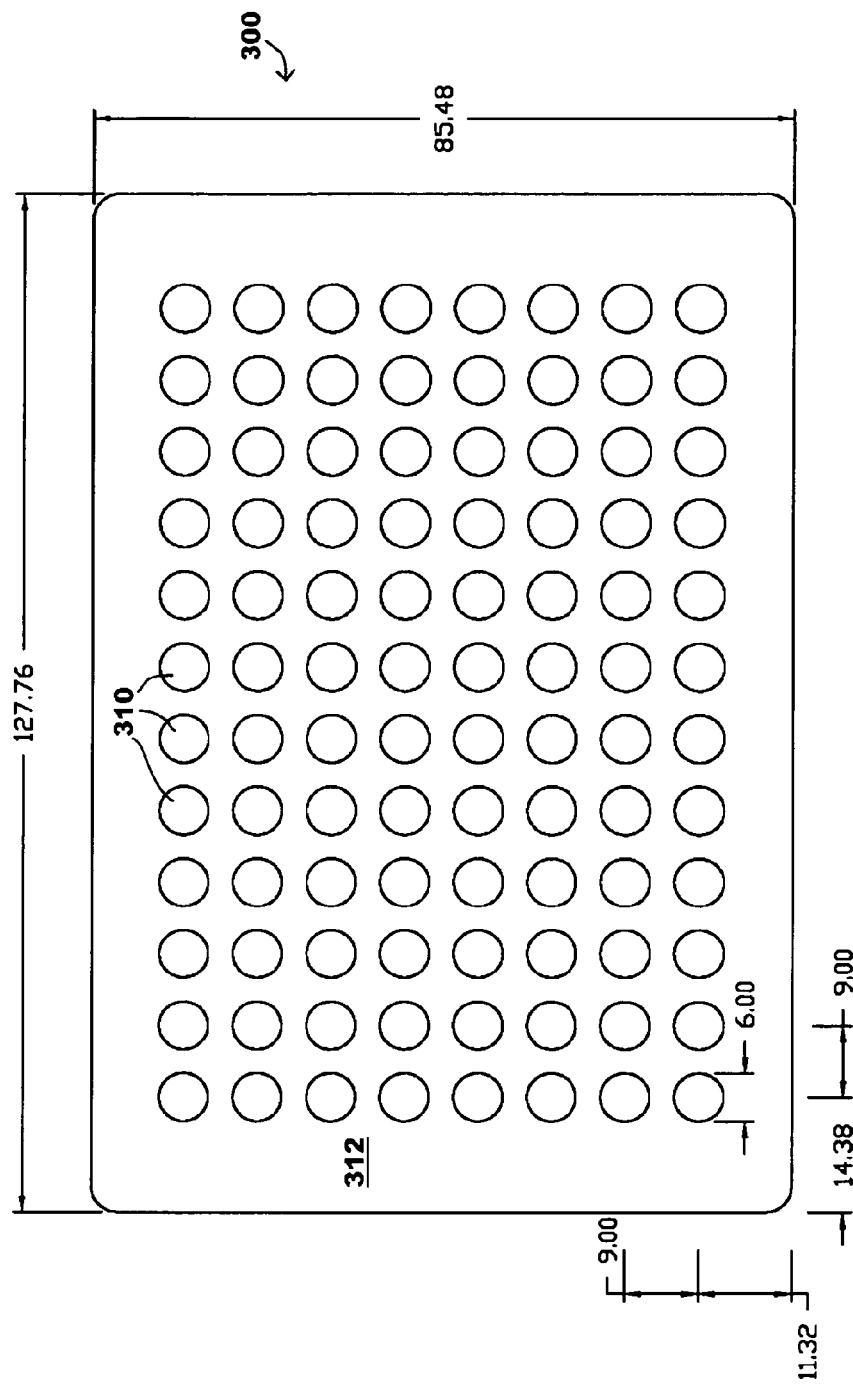

OPTICAL INSTRUMENTS

TECHNICAL FIELD

This invention relates to instruments for measuring the optical properties of samples.

BACKGROUND ART

Traditional instruments for measuring the optical properties of liquid samples employ sample holders such as cuvettes, and the measurements are made on the bulk properties of the liquid.

WO 2007131945 discloses a microvolume analyser employing a drophead having a surface which is adapted to receive a drop of liquid to be tested, the drophead being positioned in use relative to a source and a detector to illuminate a drop received thereon so that the drop causes an interaction in the path of the electromagnetic radiation between the source and detector. Unlike with bulk systems, the surface of the drophead is dimensioned to constrain the drop to adopt a shape which is dominated more by surface tension forces than by gravitational forces.

Liquid drops with such small volumes cause particular considerations which do not exist for bulk volume analysers. The properties of the drop are dependent on the drop shape which is in turn dictated by the volume of liquid in the drop due to the dominance of surface tension forces over gravity. As a result, any inaccuracy in the drop volume leads to inaccuracy in measurement. A particular source of variation in drop volume is a evaporation from the drop between the time when the drop is deposited on the drophead and the time when the measurement is taken. There can be a great deal of variation in this regard, particularly if there are repeated measurements or where different operators take different measurements.

DISCLOSURE OF THE INVENTION

There is provided an optical instrument comprising:
a housing having a drop-supporting surface for receiving a droplet of liquid;
a cover having outer and inner surfaces, the cover being mounted on the housing such that the inner surface faces the drop-supporting surface of the housing;
a connector provided on the cover for receiving a light source and providing communication between the light source and the inner surface of the cover;
the cover having a loading aperture extending therethrough, the aperture being spaced apart from said connector;
a mounting provided between said cover and said housing permitting relative rotational movement between the cover and the housing about an axis between measurement and loading positions, wherein when in said measurement position the connector is positioned relative to the drop-supporting surface such that a light source received in said connector is positioned to illuminate the drop-supporting surface, and when in said loading position the loading aperture is positioned to provide access to the drop-supporting surface;
a positioning mechanism provided between said cover and said housing to engage said cover when it reaches said measurement position and thereby ensure that the light source and drop-supporting surface are maintained in fixed spaced-apart relationship.

The optical instrument provides a different approach to the problem of positioning an optical sample in position relative to a light source. Rather than providing a bulk sample in a container which is inserted into position between a source and detector, or depositing a drop onto a drophead below a light source, the instrument provides a drop-supporting surface carried upon a housing, with the light source being carried into and out of position on a rotating cover. The cover is designed to reveal the drop-supporting surface through an aperture when in a loading position and to conceal the drop-supporting surface when in a measurement position, and furthermore, a mechanism is provided to positively engage the cover and housing into that measurement position to ensure accurate positioning of the source and droplet.

In addition, the use of a connector receiving the light source and providing communication to the inner surface of the cover, in combination with the cover being rotatable into and out of the measurement position, provides a way of isolating the droplet from ambient light below a cover without having to manipulate the drop once it has been deposited (bearing in mind that the apparatus is preferably for use with microliter sized droplets, more preferably in the range 1-5 microliter with a particularly preferred embodiment having a 2 mm diameter plinth which receives droplets of approximately 2-3 microliter).

The connector may be wholly internal to the cover, i.e. a mounting provided within the cover for a self-contained light source such as an LED, or it may be a conduit extending through the cover to enable an external light source to illuminate the drop-supporting surface through the cover.

Preferably, said mounting further permits translational movement between the cover and the housing along said axis, and the positioning mechanism is arranged to engage and hold the cover relatively closer to the housing when in said measurement position and to cause the cover to move relatively further from the housing when the cover rotates relative to the housing away from said measurement position.

This provides a way of maximising the exposure of the droplet to the light source when in the measurement position, by bringing the connector axially closer to the droplet, while moving the connector away from the droplet when rotating the cover.

Further, preferably, the positioning mechanism comprises means for biasing the cover towards the housing along said axis.

Even more preferably, the positioning mechanism further comprises complementary shaped features provided respectively on said cover and said housing, said complementary shaped features permitting the cover and housing to move closer together under the action of the biasing means when the cover is rotated relative to the housing to the measurement position, and forcing the cover and housing apart against the biasing means when the cover is rotated relative to the housing away from the measurement position.

In a preferred embodiment the complementary shaped features are a projection on one of the cover and housing and a recess on the other of the cover and housing, wherein the recess is dimensioned and positioned relative to the projection, when the cover is in the measurement position, to at least partially receive the projection, and when the cover is rotated relative to the housing away from the measurement position the projection moves out of the recess and forces the cover and housing apart.

The projection may be provided by a ball bearing mounted in and protruding slightly from one of the cover and housing and a recess provided in the other of the cover and housing, so that when the bearing and recess are aligned the cover and housing can move closer together than when they are not aligned and the bearing forces the cover and housing further apart.

In preferred embodiments, the housing and the cover are mutually shaped, in the vicinity of the drop-supporting surface and the connecter respectively, to define a chamber which encloses said drop-supporting surface with said connector being in optical communication with the chamber when the cover is in the measurement position, the chamber opening when the cover is rotated relative to the housing to the loading position to reveal the drop-supporting surface through the aperture.

This arrangement is particularly advantageous as it encloses the drop-supporting surface in a chamber, thereby isolating it for measurement. In addition to isolating it physically to avoid disturbing the droplet, the chamber is preferably defined by opaque walls so that the only light reaching the droplet is from the source attached to the connector.

The chamber is preferably sealed such that the droplet is surrounded by a relatively small air volume. This assists in reducing the evaporation both due to the atmosphere becoming saturated and the air around the droplet being still.

The volume surrounding the drop can also be sealed to stop contamination of the working environment by toxins such as dangerous medical or biological organisms.

Preferably, the chamber further includes a receptacle for a liquid volume, spaced apart from the drop-supporting surface.

When liquid is present in such a receptacle, evaporation of the liquid assists in saturating the volume of air in the chamber, which in turn reduces evaporation from the droplet.

In a preferred embodiment, the receptacle for the liquid volume comprises a moat surrounding the drop-supporting surface.

The instrument preferably further comprises a seal provided on one of the housing and the cover to seal said chamber and isolate it from the atmosphere.

Preferably, in addition to said loading aperture in said cover, a second loading aperture is provided in said cover, such that from the measurement position the cover may be rotated relative to the housing in one direction to reveal the drop-supporting surface through the loading aperture in said loading position and in another direction to reveal the drop-supporting surface through the second loading aperture in a second loading position.

Providing a pair of loading apertures in the cover, each of which is positioned to reveal the drop-supporting surface when the cover is rotated in a different direction, assists in use of the apparatus by both left- and right-handed operators, or by an operator using either left or right hands, where the other hand is occupied.

The instrument preferably further comprises a limiting mechanism provided between the housing and cover to restrict the rotation of the cover relative to the housing.

There is also provided a method of measuring an optical property of a liquid droplet, comprising the steps of:
 depositing said droplet on a drop-supporting surface through a loading aperture of an instrument cover rotationally mounted on an instrument housing, said loading aperture providing access to the drop-supporting surface when the cover is in a loading position;
 rotating said cover to a measurement position wherein when in said measurement position a light source providing illumination to on an inner surface of the cover is positioned to illuminate the drop-supporting surface, and wherein when in said measurement position the light source and drop-supporting surface are maintained in fixed spaced-apart relationship.

There is also provided the use of an optical instrument as aforesaid comprising the steps of loading, rotating and measuring as described herein.

There is also provided a drophead for supporting a droplet to be analysed, comprising a drop-supporting surface for receiving a droplet, a reservoir for holding a liquid solvent, and a separating surface isolating the reservoir from the drop-supporting surface.

Preferably, the reservoir is in the form of a moat surrounding the drop-supporting surface.

Preferably, the moat is annular and the drop-supporting surface is at the centre of the annulus.

Preferably, the drop-supporting surface is a face of a raised cylinder and the separating surface is an annular surface surrounding the cylinder and is itself surrounded by the reservoir.

Preferably, the drop-supporting surface is of a dimension sized to stably support thereon a droplet of no greater than 5 microliter.

Preferably, the drop supporting surface is a face of a first quartz member.

Further, preferably, the surrounding surface is a face of a second quartz member.

Preferably the first quartz member is substantially transparent to visible radiation.

Preferably the second quartz member is substantially opaque to visible radiation.

Preferably the first quartz member is a cylinder and the second quartz member is an annular disk surrounding the cylinder.

In an alternative preferred embodiment a plurality of said drop-supporting surfaces are provided on a body such that each drop-supporting surface is surrounded by a reservoir.

Preferably, a single reservoir is provided within which a plurality of raised formations are provided with each raised formation providing a separating surface isolating the reservoir from one or more drop-supporting surfaces located on the raised formation.

In a preferred embodiment, each drop-supporting surface is provided on a separate raised formation and said raised formations are provided in an ordered array within the reservoir.

Preferably, such a drophead, in which the raised formations are provided in an ordered array, is configured as an assay plate for receiving a plurality of droplets for analysis in a plate reader.

There is also provided a method of using a drophead as aforesaid in an optical instrument comprising the steps of depositing a droplet on the or each drop-supporting surface (or a subset thereof), and adding a liquid to the reservoir to inhibit evaporation of said droplet(s) by generating an increased level of vapour saturation in the vicinity of said droplet(s).

There is also provided an optical instrument comprising a drophead as aforesaid, a source and a detector adapted to be positioned relative to the drophead to respectively illuminate and detect illumination coupled into a droplet loaded on the drop-supporting surface.

Preferably the optical instrument further comprises a sealing mechanism to provide a sealed chamber in which the reservoir and droplet are located in use when the source and detector are in a measurement configuration.

BRIEF DESCRIPTION OF THE DRAWINGS

FIG. 4 is a perspective view of the top surface of the housing of the instrument of FIG. 1, with cover removed;

FIG. 5 is a perspective view of a threaded, spring-loaded, spindle component of the instrument of FIG. 1;

FIG. 6 is a partial cross-sectional elevation through the upper part of the instrument of FIG. 1;

FIG. 7 is a view similar to FIG. 6 but with the cover shown in a loading position;

FIGS. 8, 9 and 10 show the instrument of FIG. 1 in a plan view from above, respectively showing the cover in a first loading position, a second loading position; and a measurement position;

FIG. 27 is a bottom plan view of the well plate of FIG. 24.

DETAILED DESCRIPTION OF PREFERRED EMBODIMENTS

Figure 1:
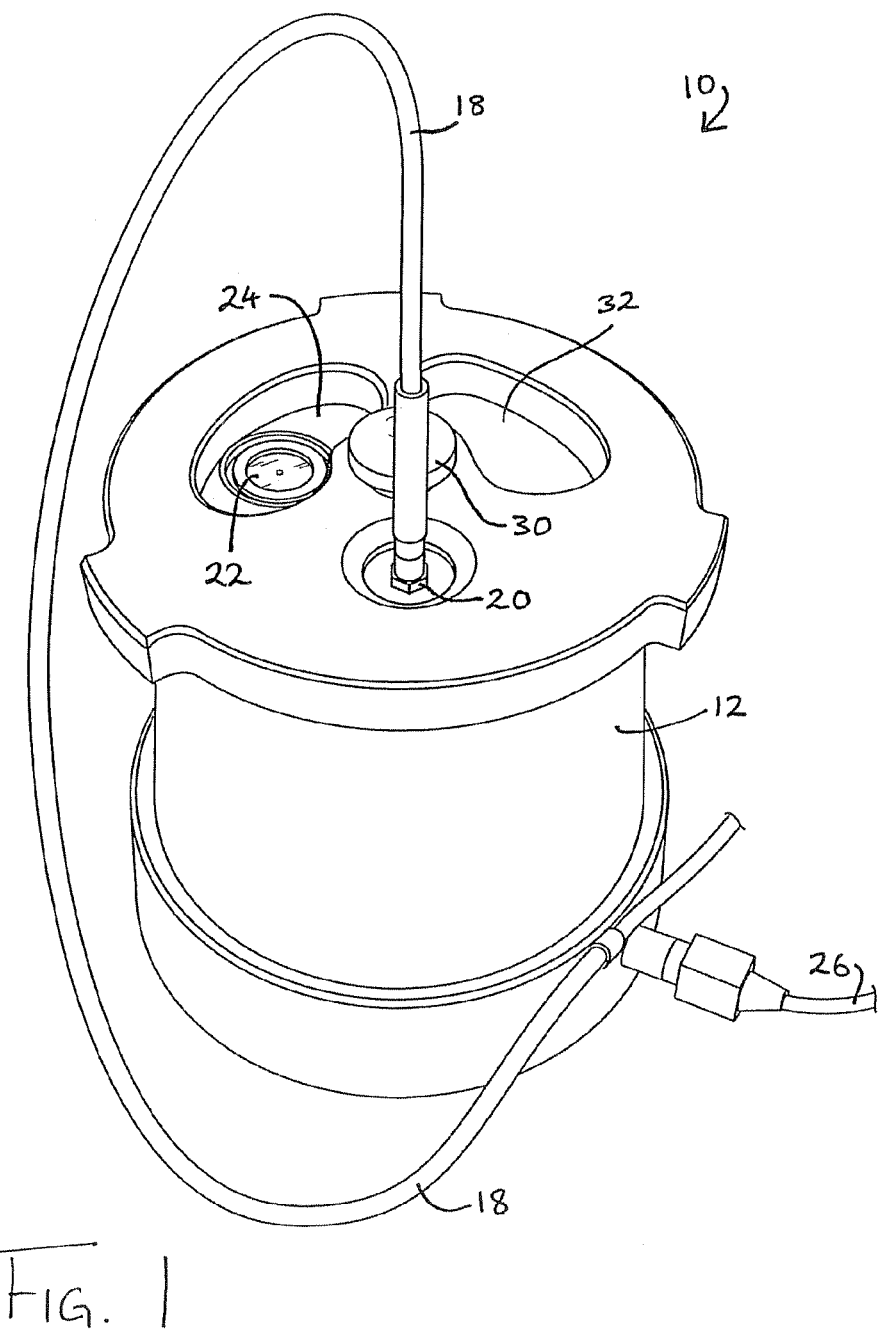
FIG. 1 is a perspective view of an optical instrument according to the invention.

In FIG. 1 there is indicated, generally at 10, an optical instrument comprising a housing 12 having a base 14 and a cover 16 rotatably mounted on the housing. An optical fiber sheath 18 carries an optical fiber providing a light source is received in a connector 20 provided in the cover. A drophead assembly 22, which will be described below, is visible and accessible through an aperture 24 provided in the cover 16. The fiber optic light source may be replaced by any other suitable source such as an LED integrated into the cover.

The instrument operates generally by loading a liquid sample droplet on the drophead assembly 22 via the aperture when the cover is in the loading position shown in FIG. 1, then rotating the cover 16 to a measurement position so that the connector 20 is positioned directly above the drophead assembly 22. The liquid sample drop on the drophead assembly 22 is illuminated from above by the fibre optic cable 18. A detector (not visible) is positioned below a transparent part of the drophead assembly to collect and measure light interaction with the liquid sample. The measured light is converted to an electronic signal which may be optionally pre-processed on board the instrument 10, and the resulting signal is output via a signal cable 26 for analysis.

Figure 2:
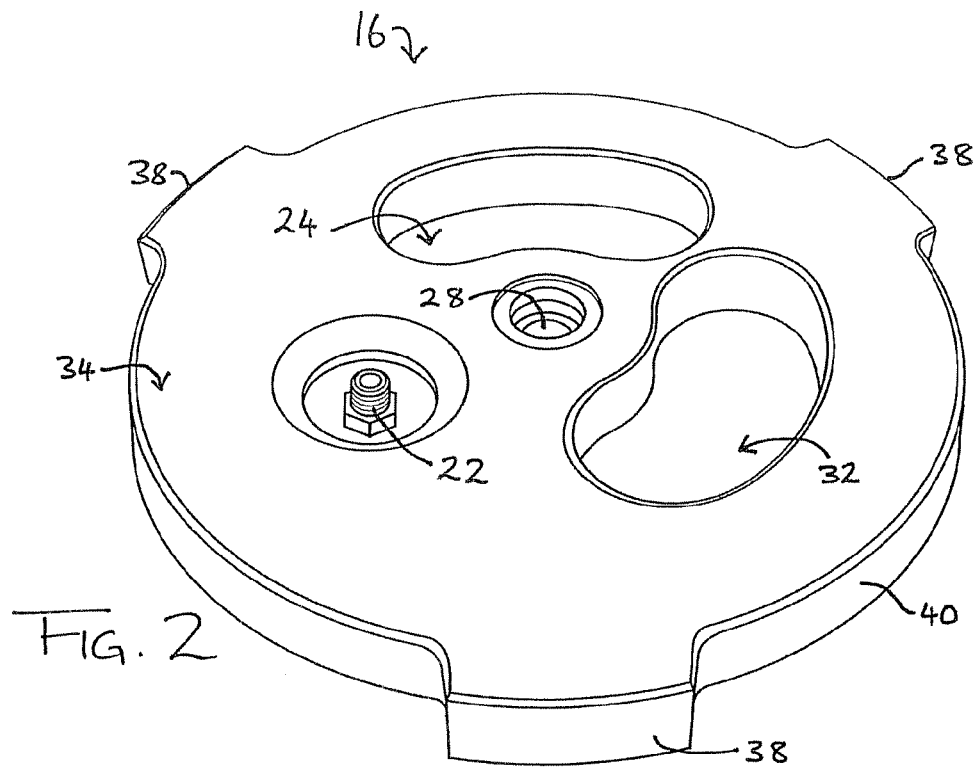
FIG. 2 is a perspective view of the cover of the instrument of FIG. 1, taken from above.
Figure 3:
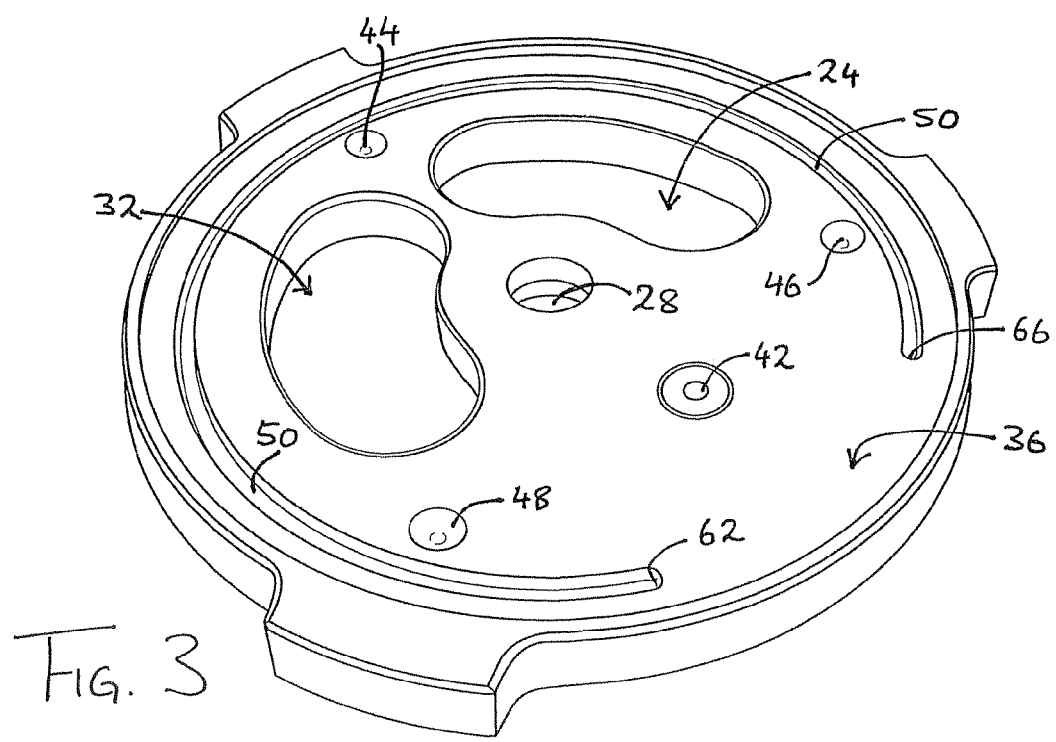
FIG. 3 is a perspective view of the cover of the instrument of FIG. 1, taken from below.

The cover is shown in more detail in FIGS. 2 and 3 from above and below, respectively. The cover 16 takes the general form of a flat cylinder or disk. A central hole 28 is provided to receive a spindle 30 (FIG. 1) about which the cover rotates when mounted on the housing 12. A pair of kidney-shaped apertures 24, 32 extend through the cover between the outer surface 34 (FIGS. 1 and 2) and inner surface 36 (FIG. 3) of the cover 16.

The apertures 24, 32 are dimensioned and spaced radially from the central hole 28 to overlie the drophead assembly 22 (FIG. 1) when the cover is rotated to the appropriate angular positions. Similarly, the connector 22 is radially spaced from the central hole 28 such that it too will overlie the drophead assembly when the cover is rotated to the appropriate angular position. A set of three lugs 38 around the perimeter 40 of the cover 16 are provided to assist in manipulation of the cover by rotation.

The connector 22 is set into a depression in the outer surface of the cover to ensure that when an optical fiber 18 (not shown in FIGS. 2 and 3) is connected to the connector 22 the termination of the fiber is flush with the inner surface 36.

On the inner surface (FIG. 3) one can see, in addition to the apertures 24, 32 and central hole 28, a receiving hole 42 through which a fiber end emerges.

Also visible on the inner surface are a series of three equi-angularly spaced depressions 44, 46, 48 (i.e. angularly spaced at 120 degrees from one another) which are each dimensioned to receive a ball bearing mounted on the housing as will be described further below. Also visible and described further below is a circumferential groove 50

Referring additionally now to FIG. 4, one can see the top surface 52 of the housing 12 when the cover has been removed. The drophead assembly 22 can be seen and one can also see a set of three ball bearings 54, 56, 58 each of which is captured in the top surface of the housing such that the cover slides along the top of the ball bearings. The bearings are also equi-angularly positioned and are located such that when the cover is in the measurement position the ball bearings 54, 56, 58 are received in the depressions 44, 46, 48 (FIG. 3) as follows: depression 44 receives bearing 54; depression 46 receives bearing 56; and depression 48 receives bearing 58.

If the cover is rotated from the measurement position to one loading position by a 120 degree counter-clockwise rotation (this being the position shown in FIG. 1), then depression 44 now receives bearing 56 and so on. Further rotation in the counter-clockwise direction is prevented by the interaction of a first pin 60 (FIG. 4) with a stop 62 provided by one end of groove 50 (FIG. 3).

If the cover is then rotated clockwise through 120 degrees one again reaches the measurement position, and a further 120 degree clockwise rotation results in a second pin 64 reaching a stop 66 at the other end of the groove 50 and the depression 44 receiving bearing 58.

When the cover is in an intermediate position between the central measurement position and either of the loading positions either 120 degrees to clockwise or 120 degrees to counter-clockwise, the bearings 54, 56, 58 are not located in any of the depressions 44, 46, 48 but instead bear against the inner surface 36 (FIG. 3) of the cover along the notional circumferential track (not shown) located just inside the circumferential groove 50 upon which each of the depressions 44, 46, 48 lies.

Referring additionally to FIG. 5, one can see a spindle member 68 carrying a spring 70 and having a domed head 72, spindle shaft 74 and terminal screw thread section 76.

Referring additionally to FIG. 6, the complete assembly of the spindle member 68, cover 16 and top surface of housing 52 can be seen in cross sectional elevation along a line taken through the drophead assembly 22, bearing 54 and a central threaded hole 78 visible in FIG. 4 which receives the screw thread section 76 of spindle member 68.

In FIG. 6, the cover 16 is rotated to the measurement position. Therefore, it can be seen that the inner surface 36 of cover 16 and the top surface 52 of the housing are in close proximity, due to the bearing 54 being received in the depression 44 (and indeed the other two bearings 56, 58 which are not visible being received in the other two depressions 46, 48 respectively). The cover is biased downwardly into contact with the housing by the spring 70 which urges the cover 16 away from the dome 72. While FIG. 6 appears to show the inner surface 36 and top surface 52 in contact they are in fact spaced slightly apart across the majority of their area but with a sealing contact around the connector 20 and drophead assembly 22 as will be described further below in relation to FIG. 11.

As can be seen, in the measurement position, the optical fiber 18 is positioned directly over the drophead assembly 22. The use of a set of three bearings which closely fit into three depressions when the cover reaches the measurement position results in a very precise and positive engagement of the cover into position with the optical fiber positioned directly over a drop carried on a drop supporting surface as will be shown in further detail below. The spring biasing the cover downwards results in the cover being held in this position against accidental movement and provides a small resistance against movement away from this position, so that the operator is required to positively rotate the cover to lift it over the top of the bearing surface as it starts to rotate to one or other of the measurement positions.

FIG. 7 is a view similar to FIG. 6 but with the cover shown in a loading position with a pipette 79 depositing a droplet 98 on a plinth 100 of the drophead assembly 22 through one of the kidney-shaped apertures loading apertures 24.

FIGS. 8, 9 and 10 show the apparatus in a plan view from above when the cover is in three different positions: FIG. 8 shows the cover in the first loading position (same as in FIG. 1); FIG. 10 shows the cover in the measurement position, having been rotated 120 degrees clockwise from FIG. 8; and FIG. 9 shows the cover in the second loading position having been rotated a further 120 degrees clockwise.

Figure 11:
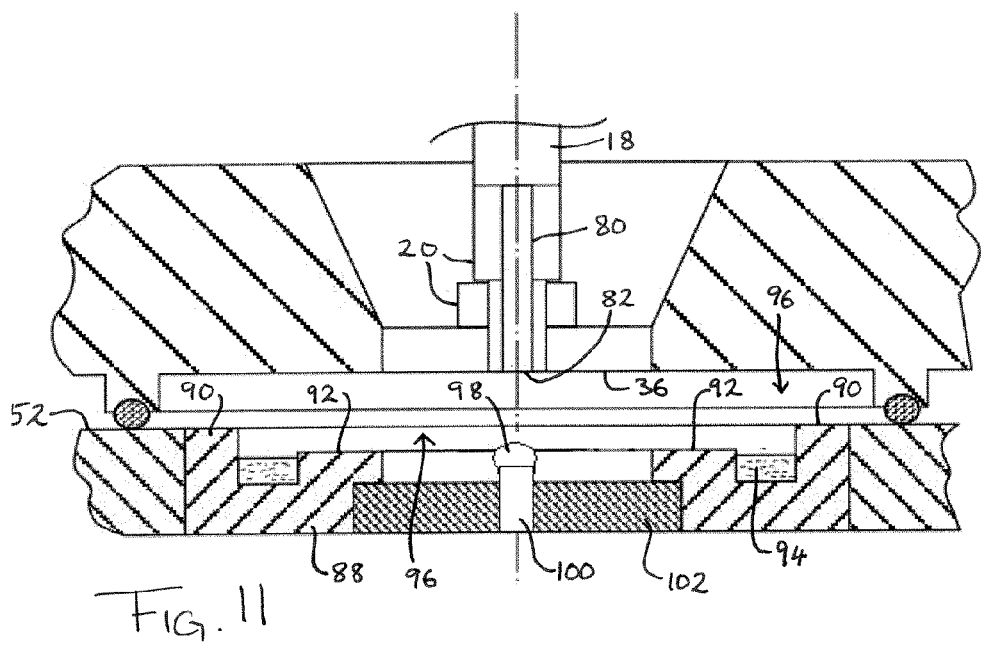
FIG. 11 is a partial cross-sectional elevation of a detail of the cover and housing of the instrument of FIG. 1.

FIG. 11 shows an enlarged view of a detail of the cover and housing, in particular showing details of the light source and connector, namely the optical fiber sheath 18, the actual fiber 80 terminating at a terminal surface 82 which carries light from an external source (not shown), and the parts of the connector 20 mating the sheath 18 to the cover 16.

The inner surface 36 of the cover 16 carries a raised circular lip 84 on which an O-ring seal 86 is mounted, so that the terminal surface of the fiber 82 is contained within and at the centre of the lip 84. Thus, the o-ring 86 makes a seal with the top surface 52 of the housing when the cover drops into position due to the depressions and the bearings being in registration and due also to the downward urging of the spring as previously described.

Figure 12:
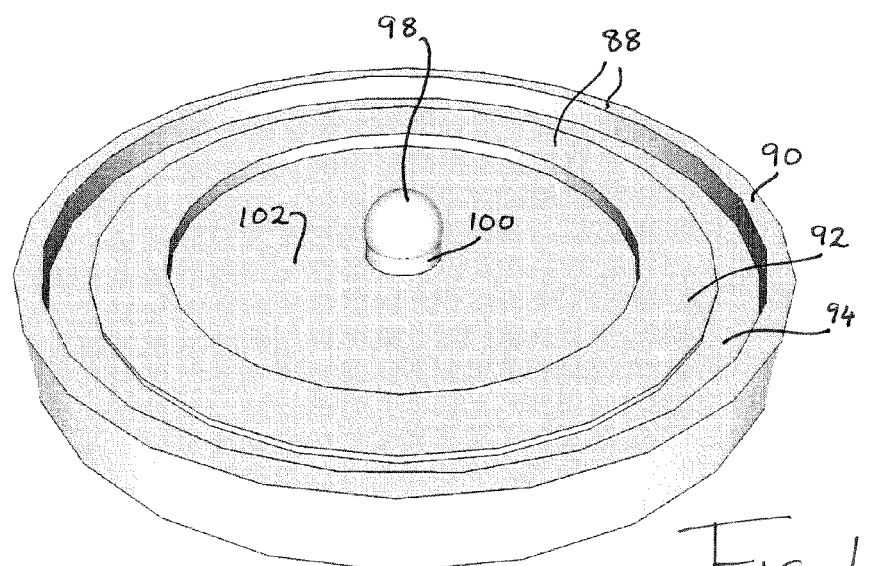
FIG. 12 is a perspective view of a drophead assembly of the instrument of FIG. 1.

Referring additionally to FIG. 12, which shows in isolation the drophead assembly 22 from FIG. 11, the details of the drophead assembly indicated generally at 22 will now be described. The assembly 22 comprises a plastic annular outer body 88 having a raised outer rim 90 and a raised inner surface 92 (lower than the outer rim). Between the outer rim 90 and inner surface 92 is an annular moat or reservoir 94 which in use is partially or fully filled with a liquid which is preferably the liquid under test (i.e. the droplet) or a major component of the liquid under test, such as being a solvent or suspending liquid used in the liquid under test. In cases where the liquid under test is a complex composition one of the major components of that liquid can be placed in the reservoir (for example, when testing wine or beer, the moat may be filled with water; when testing nail varnish, the moat may be filled with acetone).

The purpose of the liquid in the moat is to generate a more saturated atmosphere around the liquid under test and generally within the chamber 96 defined between the inner surface 36, top surface 52 and seal 86. As this chamber 96 is sealed once the cover 16 drops into place when rotated to the measurement position, and due to the small volume of the chamber 96, a vapour equilibrium is quickly established following which evaporation of the droplet is largely inhibited.

The sealed chamber can also be used to purge the samples for delivery into a sealed container to allow for safe disposal. Such a sealed chamber for sample can be used to effect control of the humidity or indeed other environmental factors such as temperature, atmospheric type for admixtures of gases or vapours for example, sterilizing UV to kill biological molecules etc.

The droplet 98 itself sits on a drop supporting surface defined by the top of a cylindrical quartz plinth 100 mounted in a black quartz disk 102. Black quartz is used as it fuses with quartz to provide an atomically bonded structure for the drophead but one that is optically differentiated from the sample head and assist the light guiding effect through the plinth between the droplet and the detector (not shown). Light shining on the droplet 98 from the fiber 80 is coupled through the quartz plinth 100 into a detector (not shown) located immediately below, or into a fiber (not shown) immediately below the plinth 100.

For a droplet whose volume is sufficiently small so that surface tension forces dominate over gravitational forces, the optical characteristics of the droplet are dependent on both the geometry of the drop and the composition of the liquid itself. For two droplets of identical volume, surface tension forces will ensure that the shapes are also identical. Thus, one can compare the optical characteristics of two drops of exactly equal volume and any differences will be due to the optical characteristics of the respective liquids, e.g. coupling efficiency, refractive index, turbidity, colour, clarity, attenuation, fluorescence, etc. Two geometrically identical drops will have unique optical fingerprints if their composition is different, and thus by illuminating the two droplets with suitable light and measuring the transmitted light tot the detector, useful analysis can be carried out.

The technique just described is dependent, however, on the shapes of the droplets being identical at the time when the measurements are taken. While it is certainly possible using normal, careful laboratory techniques and apparatus to deposit identical small volumes of liquid to the required degree of accuracy, and while this will inevitably result in droplets of identical shape and size (leaving aside any grossly different liquids with majorly different surface tension characteristics), inaccuracies can arise if the liquid in the droplet evaporates between its deposition on the plinth and the measurement taking place. In practice interruptions and other factors may cause the delay between deposition and measurement to vary widely from one measurement to another, and if no precautions exist to prevent evaporation, this can result in the introduction of significant inaccuracies.

The moat 94 and the sealing of the chamber 96 can eliminate these inaccuracies or at least render them insignificant. Once the chamber 96 is sealed, a vapour equilibrium is quickly established following which evaporation of the droplet is largely inhibited. Thus, a long delay in taking a measurement or series of measurements does not matter because the droplet volume is stabilised against evaporation due to the vapour pressure arising from the relatively large volume of liquid in the moat saturating the volume of air in the chamber.

Figure 13:
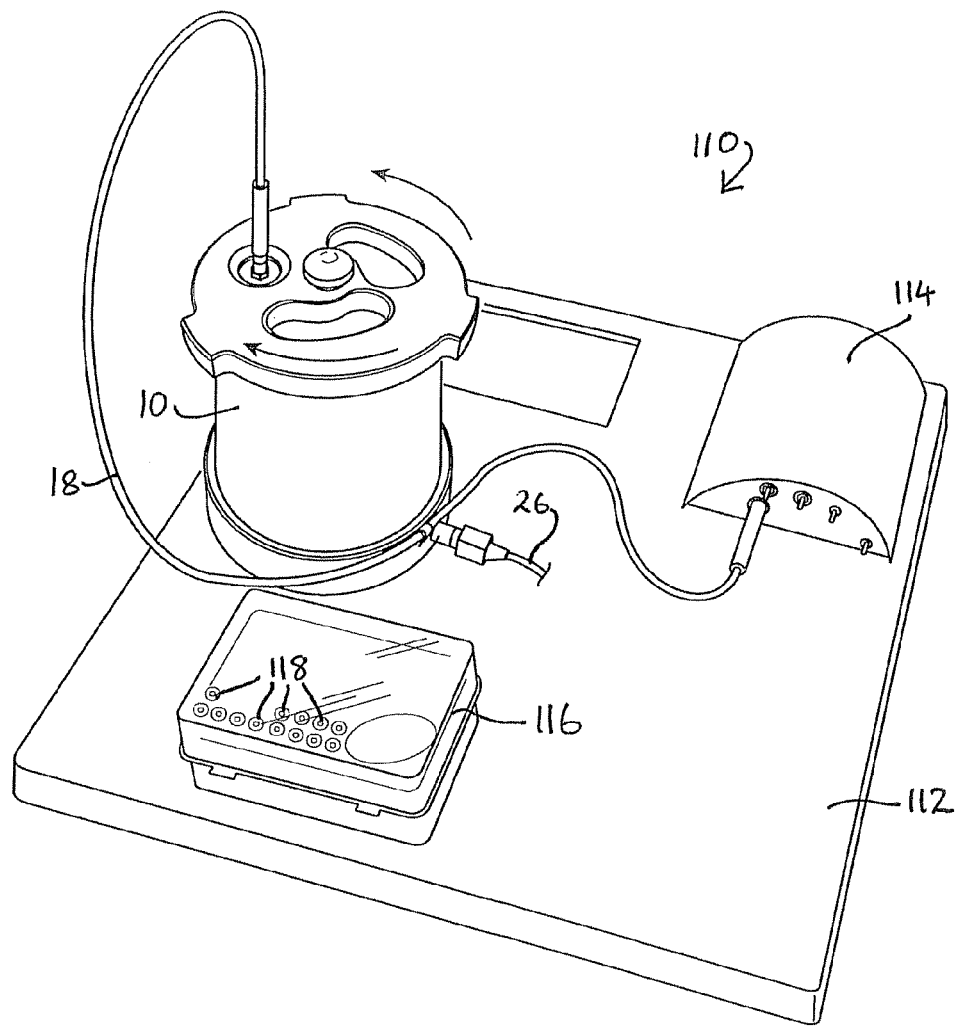
FIG. 13 is a perspective view of an optical measurement system including the instrument of FIG. 1.

FIG. 13 shows an optical measurement system 110 comprising the apparatus 10 of FIGS. 1-12 mounted on a board 112 having a light source 114 mounted thereon to which the optical fiber sheath 18 is connected. Light source 114 can be customised to provide light (which term as used herein encompasses visible, infrared ultraviolet and even microwave radiation) having any desired characteristics. The output signal cable 26 is not shown as connected to any analysis device, but in practice this may be connected to a computer running suitable analysis software to determine from the output signal the required optical characteristics of the droplet under test. Also provided on the board 112 is a container 116 for pipette tips 118 so that these can be kept in a covered location within easy reach of the operator.

Figure 14:
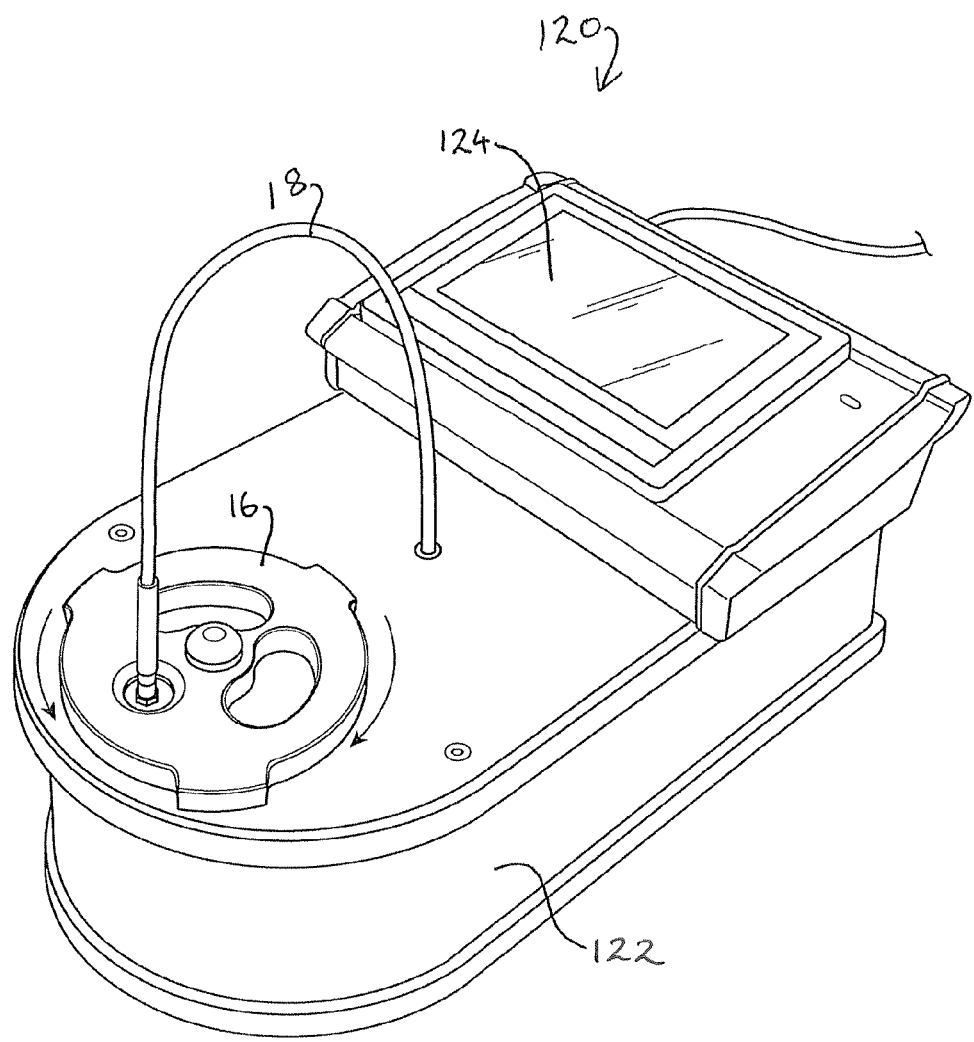
FIG. 14 is a perspective view of a further optical measurement system incorporating an optical instrument according to the invention.

FIG. 14 shows a fully integrated instrument, indicated generally at 120, having a housing 122 with a cover 16 (as previously described) mounted thereon and receiving a fiber optic sheath 18. The instrument 120 includes within the housing 122 an onboard light source, detector, and programmable electronics to control the source and the detector based on inputs provided by an operator at a touch screen 124. The programmable electronics are provided by an general purpose computer suitably programmed to interface with the source and the detector, whereby the operator may control the generation of light from the source to the fiber, the operating characteristics of the detector and the collection of data based on the detected light emerging through the plinth as previously described. The computer may be programmed with suitable analysis software to characterise and compare the output signals.

Figure 15:
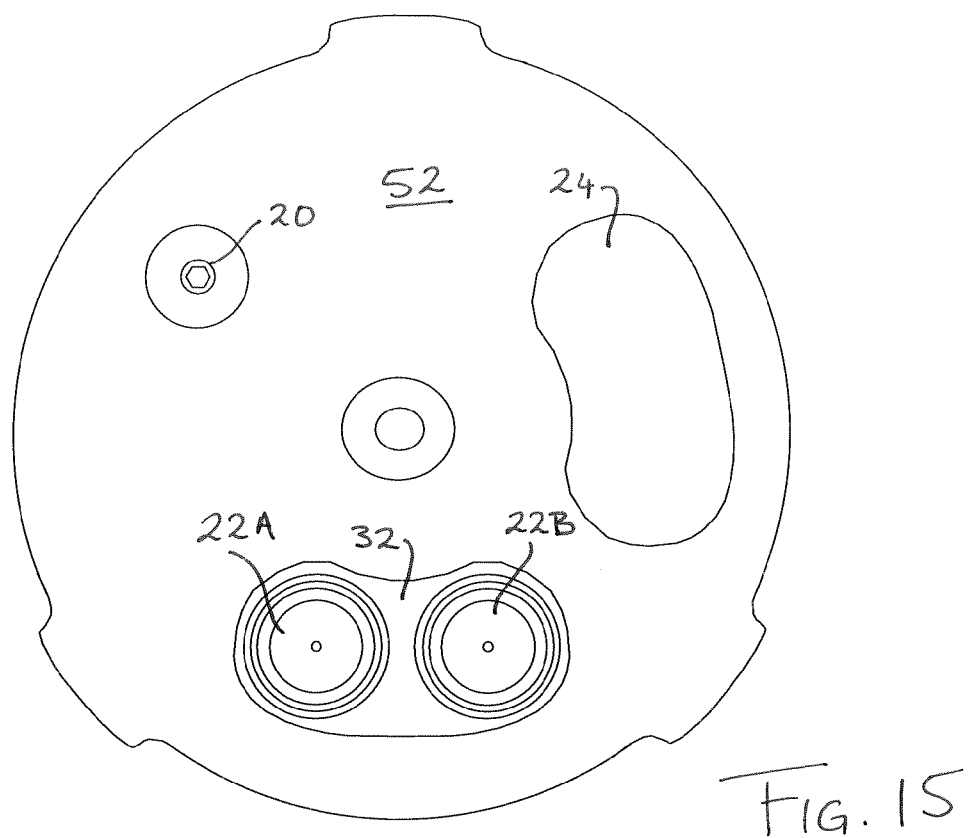
FIG. 15 is a plan view from above of an alternative embodiment of optical instrument according to the invention.

FIG. 15 shows a further instrument, in plan view from above. The instrument differs from that of FIG. 1 in two major respects.

Firstly, a pair of drophead assemblies 22A, 22B are disposed on the top surface 52 of the housing and the apertures 24, 32 are shaped and sized to allow both drophead assemblies 22A, 22B to be simultaneously revealed. This permits an operator to load both dropheads at once. As with the FIG. 1 embodiment, the provision of two apertures enables the cover to be rotated in either direction from the measurement position to allow loading.

Secondly, the positioning mechanism of the ball bearings and recesses has been modified in the FIG. 15 embodiment to provide two stable loading positions, where the connector 20 is brought into registration with one or other of the drophead assemblies 22A, 22B. Thus in the first loading position, the cover drops down (by a ball bearing locating in a recess) and a seal is made to define a chamber (as in FIG. 11) in which the fiber is positioned over the drop-supporting surface of a plinth on the first drophead assembly 22A. In the second loading position, the cover similarly drops down (by a ball bearing locating in a recess) and a seal is made to define a chamber (as in FIG. 11) in which the fiber is positioned over the drop-supporting surface of a plinth on the second drophead assembly 22B. Preferably, the cover is provided with a further pair of circular seals on the inner surface, identical to the seal 86 of FIG. 11, so that when the seal 86 is positioned around one of the dropheads 22A, 22B, the other drophead is also in a sealed atmosphere below the cover. In this way, the drophead which is not being measured is nevertheless in a sealed condition with a saturated atmosphere around the droplet to prevent evaporation.

The apparatus of FIG. 15 thus allows two samples to be loaded one after another on identical dropheads 22A, 22B as part of a single loading operation, and also allows the measurement of these two samples to take place one after another without any further interference with the samples or the dropheads. In this way, a control and an unknown sample can be loaded side by side and tested under identical conditions at almost the same time and without any possibility of the drophead being contaminated between the two samples, thereby allowing reliable and repeatable comparisons to be made with increased accuracy and decreased possibility of error.

Figure 16:
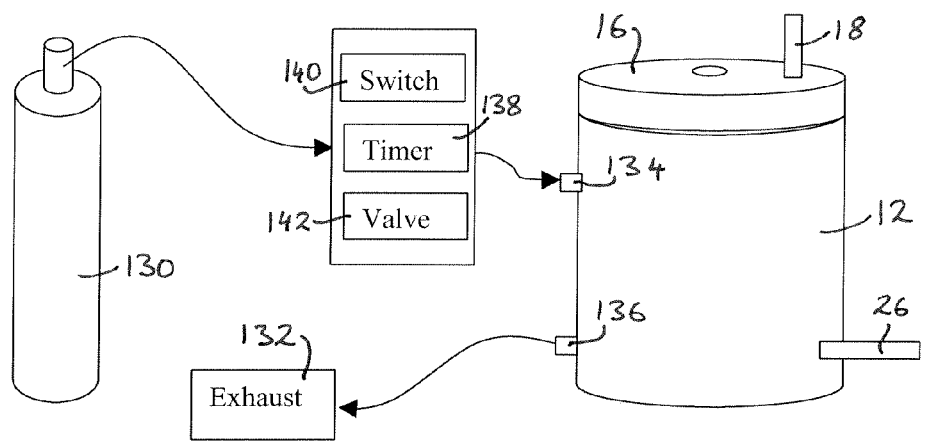
FIG. 16 is a schematic view of a modification to the instrument of FIG. 1.
Figure 17:
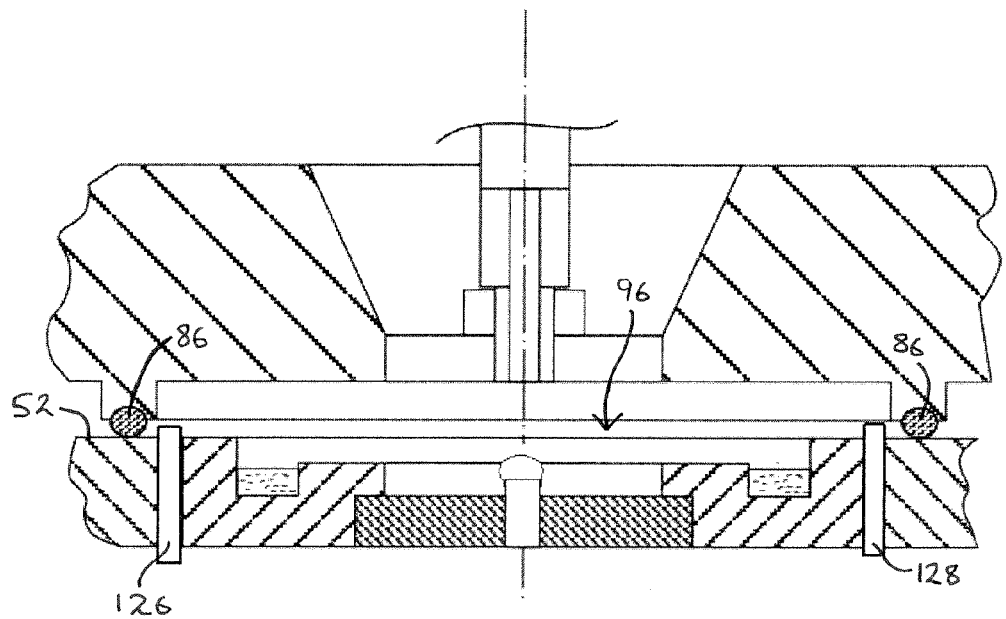
FIG. 17 is a partial cross-sectional elevation of a detail of the cover and housing of the modified instrument of FIG. 16.

FIGS. 16 and 17 shows a modification to the instrument of FIG. 1 (this modification can also be made to any of the other embodiments). FIG. 16 shows the overall system including the housing 12 which is identical to that of FIG. 1 except for the modifications now described. FIG. 17 is a view similar to that of FIG. 11.

It will be seen in FIG. 17 that there are a pair of conduits 126,128 passing through the top surface 52 of the housing inside the circular seal 86 and thus leading to the sealed volume of air within the chamber 96. Conduit 126 is an inlet conduit connected to a pressurised cylinder 130 (FIG. 17) of a purge gas such as nitrogen or helium. Conduit 128 is an outlet conduit connected to atmosphere or to an exhaust system 132 such as a fume cupboard. Typically both the inlet and outlet conduits will lead to external connectors 134,136 on the exterior of the housing 12 to which the pressurised cylinder 130 and exhaust system 132 (if required) may be connected. Finally, a simple valve 142 operated by a solenoid connected to a timer 138 may be provided to automate the operation of the cylinder on actuation by the operator of a switch 140.

Operation of the FIG. 16 system is as follows. After measuring a sample, and before rotating the cover back to the loading position (if the sample is hazardous), the switch 140 is actuated to open the valve 136 and allow pressurised gas 130 into the chamber 96. Typical gas pressure might be 1.5 bar. The pressurised gas rushing from the inlet conduit 126 to the outlet conduit 128 will sweep away the droplet on the drophead, so that the sample is sucked out of the chamber 96. After a predetermined time the solenoid will deactivate, closing the valve, following which the cover may be rotated to the loading position reveal the plinth without any droplet. Typically, the operator will wipe the drophead with a tissue to remove any final residue, ready for the next sample. The skilled person will be aware that it is possible to automate this system to any desired extent, such that all steps of rotation, solenoid actuation, etc. can be automatically effected.

Figure 18:
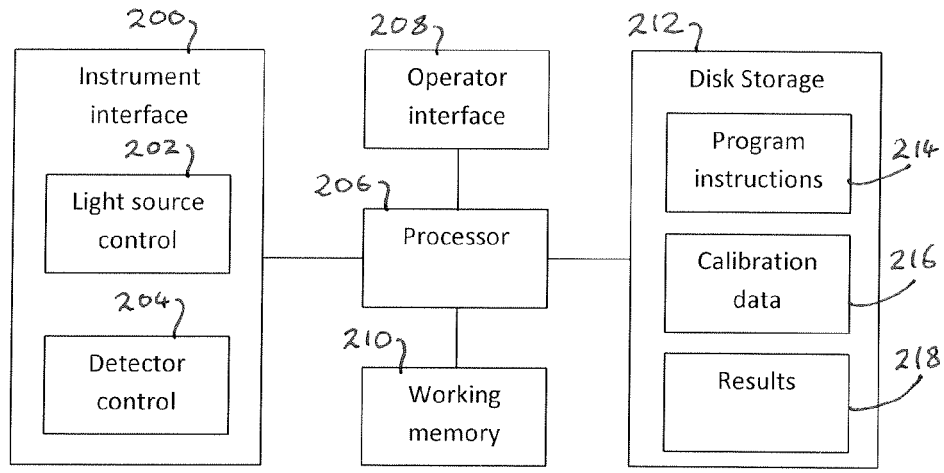
FIG. 18 is a block diagram of a control and operation system for use with an optical instrument according to the invention.

FIG. 18 is a block diagram of a control and operation system for use with any of the instruments described above. The control system interfaces with the instrument via an interface 200 having a hardware light source controller 202 and a hardware detector controller 204, which can operate the source and detector respectively within any allowed parameters.

Instructions are sent to the interface 200 from a processor 206 having an operator interface 208 and working memory 210 as well as a disk storage area 212. It will be appreciated that the processor, operator interface, working memory and disk storage can be provided as part of a suitably programmed general purpose computer or can be provided as dedicated hardware elements with a suitable operating system controlling the interaction of the components.

Program instructions 214 are stored on disk 212, and the disk 212 also stores various data elements such as calibration data 216 and results and reports 218. The operation of the system under the program instructions 214 will now be described from the point of view of the screens and controls presented to the operator via the interface 208 when the software 214 is in operation.

Figure 19:
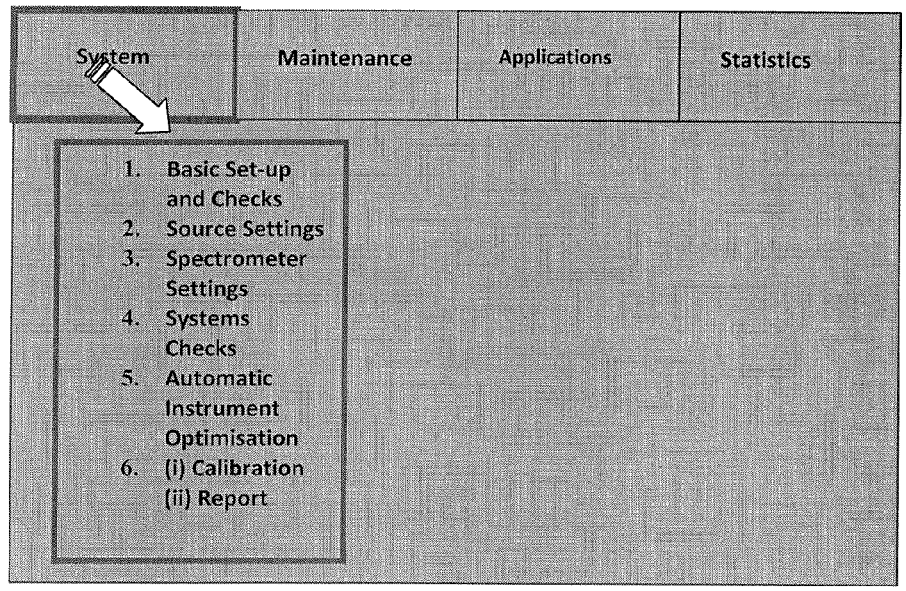
FIG. 19 is a screenshot of a user interface screen for controlling an instrument according to the invention.

The introductory screen shown in FIG. 19 includes the following tabs: system, maintenance, applications and statistics. The system tab has the menu options shown in FIG. 19, as follows:

1. Basic Set-Up and Checks

The first menu option just gives simple text instructions to ensure the user has things connected properly. This is the most elementary set-up instructions.

2. Source Checks

The adjustment of source is one that requires some basic attention and the user is given a number of diagnostic tests to ensure that the source is operational (e.g., making sure source is switched on, removing the fiber and checking light is coming from the source etc.).

3. Spectrometer Checks

The adjustment of the spectrometer depends on the type of spectrometer being used and requires attention to some settings on the software (e.g. setting integration time etc.).

4. System Checks

There are some simple checks on the system that can be conducted and here to ensure the best operation of source, drop apparatus and spectrometer (e.g., adjusting source controls and optimising spectrometer to ensure signal is not saturating). The software can direct the user to optimise the performance of the system. Selecting this option then gives user directions on adjustment of the system.

5. Calibration

Calibration standards are supplied and if these are run after the system has been optimised wavelength checks and sensitivity, linearity and reproducibility checks can be run. A service basic report is stored in the Service Archive after the measurements have been recorded and this report can be printed.

When the drop instrument is 'blanked' a spectrum is taken of a reference material and stored in memory of the computer. This data set is an array of light intensities against wavelengths assigned by the spectrometer. The intensity of source light transmitted through the drop sample is then stored for every wavelength. The corrected sample and reference intensity (Intensity minus the dark current for each wavelength) are then used to calculate the sample absorbance according to the algorithm:—

$$\text{Absorbance} = A = -\log\left(\frac{I_{sample} - I_{dark}}{I_{reference} - I_{dark}}\right)$$

The average pathlength through the drop depends on the volume of the drop and has been obtained from computer modelling of the system and also from experimental determinations based on measurements. The pathlength is determined from the software based on the volume selected. The bottom half of the screen will contain a spectra along with other relevant data for each application.

In regard to the spectrum

There is an option to save the spectrum screen as a jpg image

Allows the scale of the spectrum to change e.g. DNA only requires a wavelength range of 200-400 nm Allows spectrum overlay control (later date) where one can display more than one spectrum on the same screen display and the software allows the loading of previously recoded spectra. The spectra will be shown in different colours.

An auto-range so if this is selected it will set the grids on the screen display automatically All the settings selected will be saved on the header of the file Wavelength values where applicable can be selected using the up-down arrows to the left of the relevant box or more directly by inputting the values The calibration of the drop spectrometer is based on using a commercial standard Starna Green Calibration Fluid. Other products could be used with known spectral features and peaks with known absorbances for a given measured concentration. The absorbance values at either two or three wavelengths are returned from a measurement of the standard and compared with the known values. Replicate readings are taken and averaged and standard deviations obtained. The comparison of the standard with the known value gives a calibration of the photometric accuracy of the instrument; the standard deviation is the measure of photometric reproducibility. The analysis of the results is returned automatically in a spreadsheet as shown in the following table.

| Replicate | Absorbance (wavelength 1) | Absorbance (wavelength 2) | Absorbance (wavelength 3) | Status |
|---|---|---|---|---|
| | | | | In or out of range |
| | | | | In or out of range |
| | | | | In or out of range |
| | | | | In or out of range |
| | | | | In or out of range |
| | | | | In or out of range |
| | | | | In or out of range |
| | | | | In or out of range |
| | | | | In or out of range |
| | | | | In or out of range |
| Mean | | | | |
| Standard deviation | | | | |

The replicate number can be selected and it is advised that 10 be used as a minimum by more than 32 would be suggested based on improving the statistical validity of the tests.

The calibration tests with the drop instrument should be better than 2% accuracy and diagnostics are suggested in the software if the calibration is out to improve the measurements in a repeat calibration.

The report of the tests is filed automatically in the calibration reports file that is automatically created on the PC of the user. This report can be printed as a hard copy from the screen or from the file.

6. Automatic Instrument Optimisation

This option allows the parameters of the instrument to be automatically optimised based on the calibration results.

Referring back to the main tabs in FIG. 19, when one chooses the "Maintenance" tab the following options are presented 1. Routine Service (In-situ drophead cleaning): There are simple steps in conducting a routine service using the cleaning kit and ensuring a drop instrument can deliver good measurements not being affected for example by protein contamination.
2. Changing Drophead: A tool is provided for changing the drophead and directions are given for the existing drophead removal and its replacement.
3. Cleaning Drophead (Removed from instrument): Instructions on how to clean a drophead that has been removed from the instrument soaking in a solvent bath.
4. Changing Detector: The next option gives instructions on changing a detector (This requires the use of simple tools that are not part of the instrument kit).
5. Checking Solarisation of Fiber: The final check requires the instrument to be operational and the measurement of spectra using the calibration standards. Guidance is provided on acceptable levels of noise in the wavelength range 200-260 nm.

The "Applications" tab requires the user to select the (S) single or (D) double drop operation.

The operations are really almost the same but with deposition of two drops (sample and reference) in the latter option. The algorithms are ones that are implemented after the data acquisition to deliver results that comply with both the accepted computational methodology for these tests and complies with the accepted statistical analysis for the assay.

Taking the single drop operation as an example, the user has the following options:

1. Direct Measurement Using Calibration Graph

The standard approach to measurements in chemistry and biology is to generate a calibration graph of Absorbance against Concentration for the measurement of a dissolved component in a solution of water of some other solvent for a measurement at some selected wavelength. This Beer-Lambert calibration graph is then used to determine the concentrations of unknown solutions whose measured concentration is graphically determined from this calibration graph.

Figure 20:
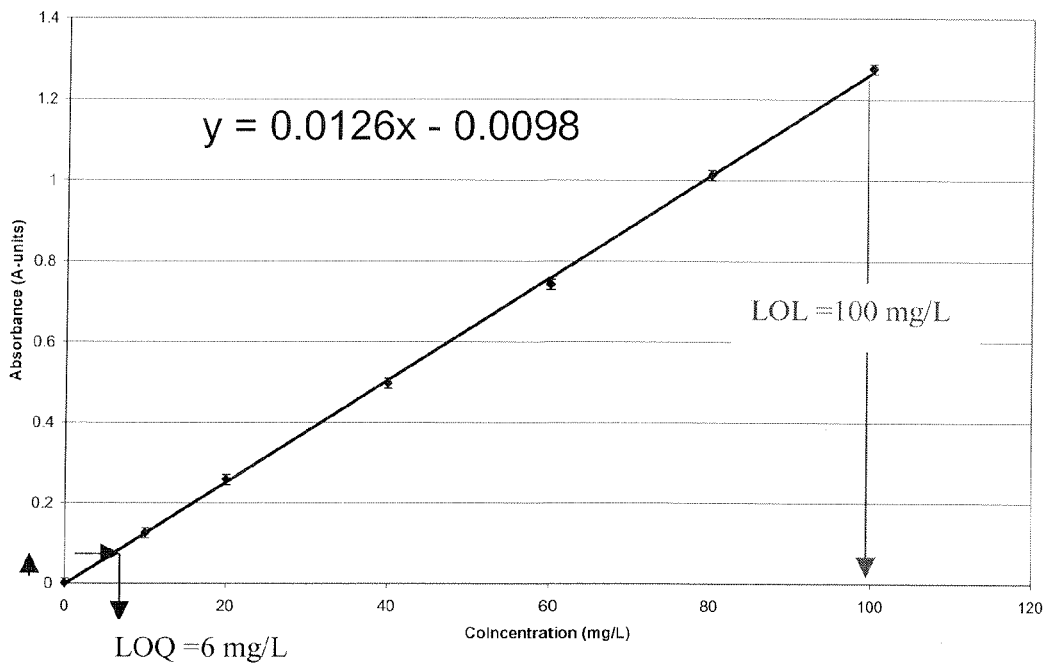
FIG. 20 is a calibration graph showing absorbance mapped against concentration.

An example is given in FIG. 20. Here the measurand is absorbance and the measurement scale is concentration. FIG. 20 shows a typical calibration and the important points to determine from the graph are (i) Calibration sensitivity (m-slope of graph)
(ii) Analytical sensitivity ($\kappa = m/\sigma_{blank}$ standard deviation of the measurand value usually taken from the blank replicate measures)
(iii) Detection limit (LOD) taken the value of the intercept projected from the measurand scale to the calibration line and down to the measurement scale for a $3\sigma_{blank}$.
(iv) The limit of quantitation (LOQ) determined in the same way but for the $10\sigma_{blank}$ intercept.
(v) Limit of linearity, determined by the variation of the fitted polynomial from a linear plot by a value exceeding $3\sigma_{blank}$.

The software offers the user the opportunity to automatically log the data without reference to any software skills with results automatically entered into the table below. The samples measured also require replicate measurements and from the advanced error analysis the values of both concentration and concentration error are returned. Checks are made immediately on the statistical acceptability of the results as the measurements proceed (see the Table below) and a tick appears after the measurements on those sets that are statistically acceptable with options offered to allow the user to repeat the calibration measurement. A tick appears in the box if the statistics show the result is acceptable. Furthermore, suggestions as to why the calibration measurements may not have been acceptable will be given without these being requested by the user who will be prompted to repeat rather than proceed with a statistically invalid result.

| Replicates | Units | 1 | 2 | 3 | 4 | 5 | 6 | 7 | 8 | 9 | 10 | Mean | σ | Pass |
|---|---|---|---|---|---|---|---|---|---|---|---|---|---|---|
| 1 | ppm | | | | | | | | | | | | | ✓ |
| 2 | ppm | | | | | | | | | | | | | ✓ |
| 3 | ppm | | | | | | | | | | | | | |
| 4 | ppm | | | | | | | | | | | | | |
| 5 | ppm | | | | | | | | | | | | | |

A results screen may also be presented which informs the user to obtain measurements of concentration between the LOQ and LOL. The data shown in FIG. 20 below gives some idea of the sort of data analysis. The values here are m=0.0126 A-units. L/mg. Here $10\sigma_{blank}=0.0756$ giving from equation LOQ=6 mg/L. The LOD is 1.9 mg/L. The graph is straight so there is no sign of non-linearity and thus we take LOL at 100 mg/L. The software returns these values using error analysis developed specially for this task.

From this graph the equations for the error-band is computed for the 3σ-error bars by the two lines displaced at an intercept on the A-axis by this range value. In the graph shown the range is $3\sigma_{blank}=0.0125$. Hence the equations for the error band is two lines $A_{top}=0.0126c+0.0027$ (obtained from [0.0125−0.0098]) and the bottom line $A_{bottom}=0.0126c−0.0223$ (obtained from [−0.0125−0.0098]). The concentration measurement is now easily computed.

The measured absorbance of the unknown is $A_{unknown}=0.464\pm0.015$ (3σ-value taken as error) giving the absorbance range of values $A_T=0.479$ to $A_L=0.449$. The calculation for the concentration of the unknown uses the equation of the best-fit line given on the graph viz. $c_{unknown}=(0.446/0.0126)+0.0098=35.41$ mg/L. The concentration error is computed from the absorbance range of the unknown measurement of concentration using the two equations for $A_{top}$ and $A_{bottom}$. The concentration range calculation is obtained substituting the $A_T=0.479$ into the equation for $A_{bottom}$ to give 38 and $A_L=0.449$ into the equation for $A_{top}$ to give 35.66.

Figure 21:
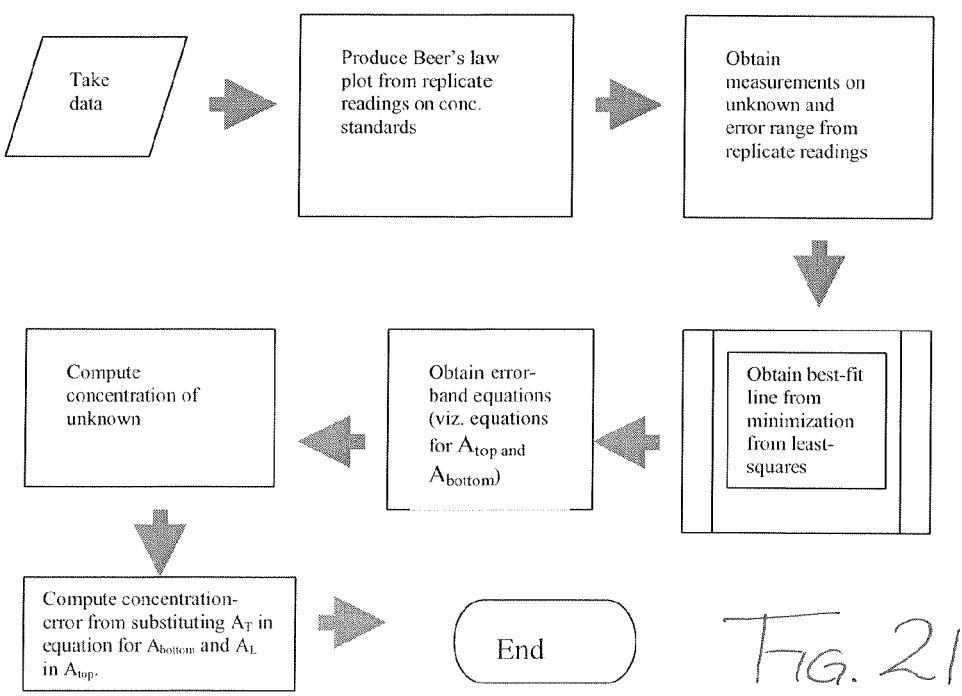
FIG. 21 is a flow diagram of an algorithm for calculating concentration from measured data.

This gives the result 35.41±2.59 (c±Δc). Actually, the errors shown here in this example of the algorithm have been exaggerated to allow error bars on the graph to be seen and these are doubled in size, so the actual real measurement obtained with these real drop analyser set of results is 35.41±1.295 mg/L. The algorithm can be described by the flow diagram of FIG. 21.

2. RNA/DNA
(i) The algorithm is based on well-established experimental relationships translated into numerical relationships. The constants differ between single and double stranded DNA and RNA. These are represented by SSDNA, DSDNA, RNA and there are indeed other nucleic acids. Select nucleic acid type.

(ii) The measurement of 'drop spectrometer' absorbance is recorded at three wavelengths 260, 280 and 320 nm.
(iii) Calculation of value to assess purity of DNA using:—

$$Purityestimate_1 = \left(\frac{A_{260} - A_{320}}{A_{280} - A_{320}}\right)$$

Pure DNA gives 1.8 and 2.0 for RNA. Lower values indicate the presence of protein or denatured DNA. There is second useful measure of purity ratio $$Purityestimate_2 = \frac{A_{260}}{A_{230}}.$$

These ratios are useful but the DNA concentration in ng/pi based on the absorbance measurements $c_{DNA}=(A_{260}-A_{320})*50*PF$ where PF=pathlength factor for the drop analyser. For example for a 3 μL drop, the pathlength equals 1.184 mm determined from modelling studies and experimental testing. The experimental study with the 2 mm diameter drophead delivered an equation for $PF=-0.0054V_D^2+0.2872V_D+0.3549$ where $V_D$ is drop volume in microlitres. The pathlength computation to convert the value to standard 10 mm pathlength absorption measurement is simply PF/10. All values reported in the drop spectrometer software are those that correspond to the values obtained with a standard spectrophotometer and a 10 mm cuvette.

(iv) Protein Assays

Figure 22:
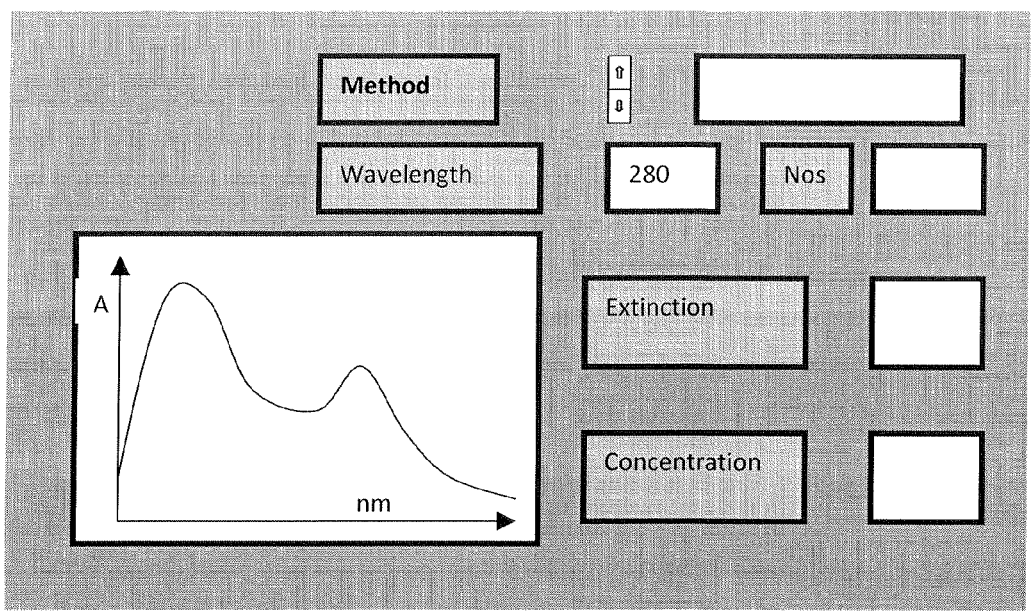
FIG. 22 is a display screen layout for presenting results for a protein assay.

The protein screen based on these measurements depends on the method selected for example a measurement at 280 nm has a screen as shown in FIG. 22.

The display of the UV-visible spectrum is presented together with:—
Measurement of absorbance at 280 nm based on the 1 cm pathlength
Inputted value of the extinction coefficient for the concentration displayed
Measurement of concentration $$Concentration = c = \frac{A_{280}}{\varepsilon \ell} = \frac{A_{280}}{\varepsilon}(Based-on-1cm-pathlength)$$

(v) BCA Assay

The BCA assay requires a standard curve to be generated each time it is run before the protein (unknown) can be measured.

The measurements are conducted at the $\lambda_{Max}$ of 562 nm and analysed at 750 nm.

Figure 23:
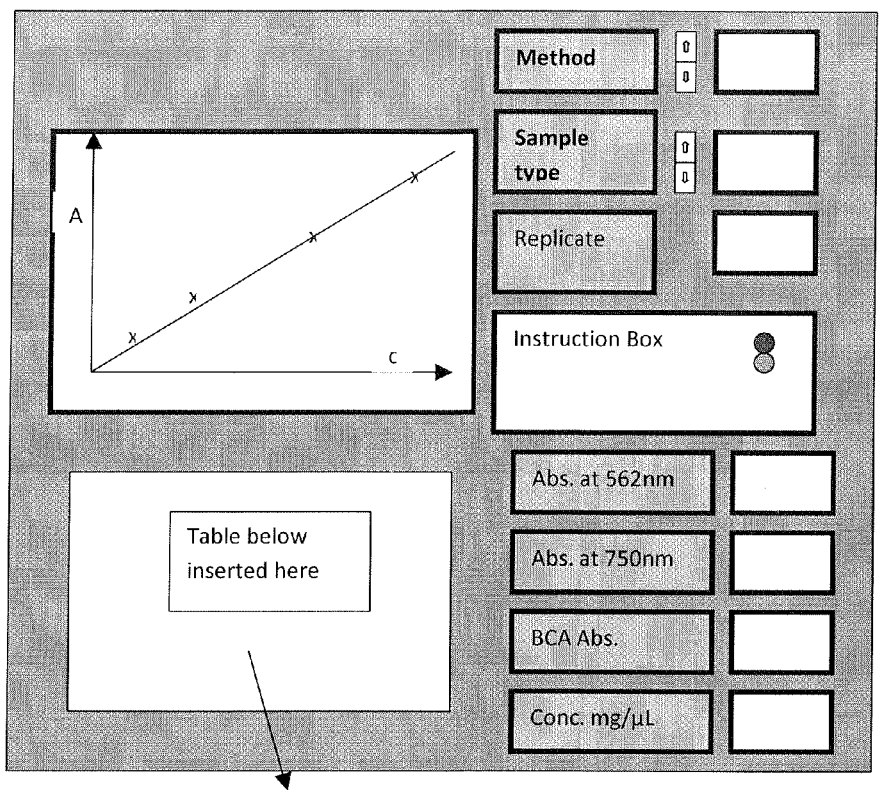
FIG. 23 is a display screen layout for presenting results for a BCA assay.

The absorbance values are proportional to the protein concentration.
Allows the user to review the standard curve at any time
The order to generate the standard curve is (i) measure the reference (BCA reagent and 'zeroed' standard.) (ii) software control will not allow measurement of less than two replicates to ensure statistical tests can be done on data (iii) user encouraged to use 5 replicates (iv) large instruction box guides user on steps in assay with traffic-light system red/green indicating when the standard curve is ready for measurement (v) HELP available to give tips to user on assay procedure FIG. 23 shows the results for a BCA assay. In relation to the calibration the user will be able to click on the table shown in FIG. 23 and delete a sample and then repeat the measurement set again. The upgraded measurement set will then be shown immediately on the graph.

Once the curve is completed the red indicator light turns green and only with this condition showing 'go' can the user begin to commence measurements.

With the green light activated the calibration graph disappears and is replaced by a spectrum screen.
Toggling option: Allows the user to review the standard curve allowing user to viewing either calibration graph or spectrum
Calibration option: Allows user to select either a previous stored calibration or to create a new one
Flexible computation option: Microdrop absorbance display at 560 nm and 750 nm based on selected pathlength (volume) with computation of absorbance based on standard 1 cm pathlength $$BCA\_Absorbance = \frac{\left(\frac{A_{560}}{\ell_{560}} - c\right)}{m}$$

NOTE: In order to obtain a concentration value in μg/mL the unknown sample must fall within the limits of the standard curve and concentration determinations are obtained by linear fitting between samples. The slope m of the standard curve (calibration sensitivity) and intercept on the calibration graph (c) is determined by software with least-squares fit.
(d) The concentration is then obtained $$Concentration = \frac{\frac{[(A_{562} * 10)]}{\ell_{562}}}{m}$$

User can select method of curve fitting required from straight-line regression; zero regression line; interpolated; and cubic-spline (vi) Lowry Assay The required standard curves are generated each run before a protein sample (unknown concentration) is measured. The sample is measured at 750 nm and normalised at 450 nm. The screen here is one shown above for the BCA but with the Lowry method box selected.

(vii) Bradford Assay

The required standard curves are generated each run before a protein sample (unknown concentration) is measured. The sample is measured at two wavelengths, 595 nm and normalised ay 750 nm. The screen here is one shown above for the BCA but with the Bradford method box selected.

(viii) Biuret Assay

The required standard curves are generated each run before a protein sample (unknown concentration) is measured. The sample is measured at two wavelengths. Measurement is at 546 nm. The screen here is one shown above for the BCA but with the Biuret method box selected.

(ii) Double Drop
1. Direct Measurements
2. DNA/RNA
3. Protein assays (i) Lowry (ii) Bradford (iii) Biuret The measurement procedures are as above but with HELP notes changed to give directions for double-drop deposition.

FIGS. 24-27 show an alternative form of drophead in the form of a microplate for use in a microplate reader shown in top plan view (FIG. 24), side elevation (FIG. 25), sectional elevation (FIG. 26, taken along the line A-A in FIG. 24) and bottom plan view (FIG. 27). The dimensions shown are exemplary only and are in mm.

Figure 24:
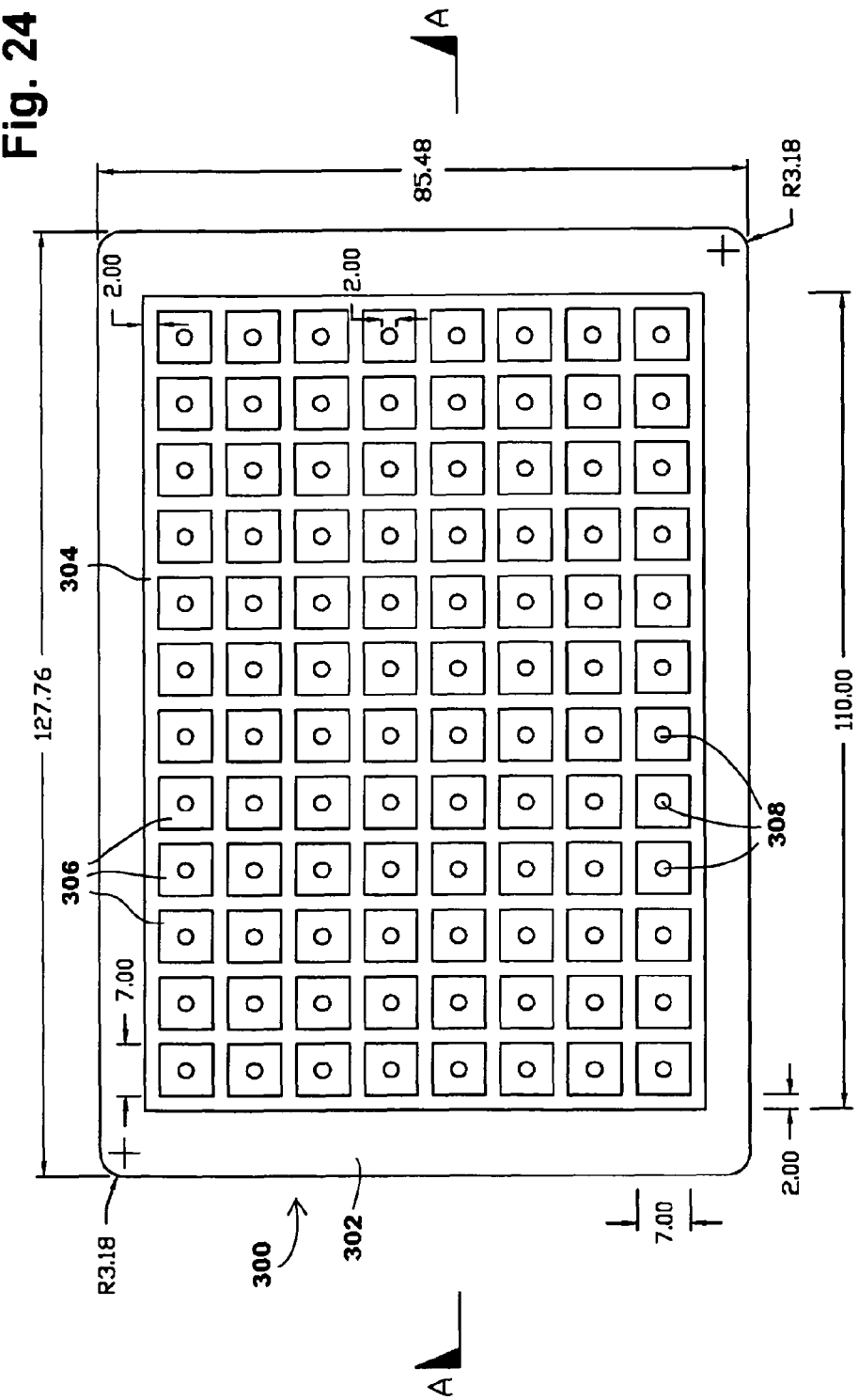
FIG. 24 is a top plan view of an alternative form of drophead assembly, provided as a well plate.
Figure 25:
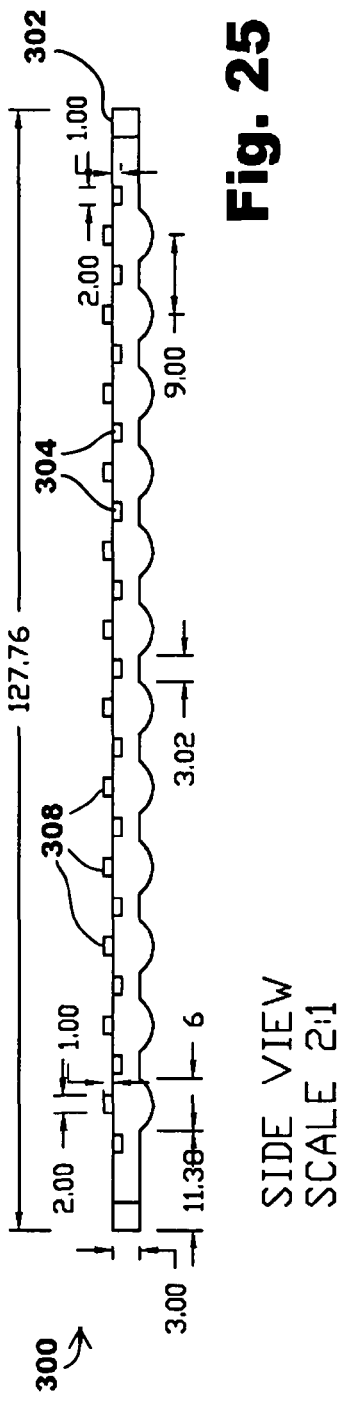
FIG. 25 is a side elevation of the well plate of FIG. 24.
Figure 26:
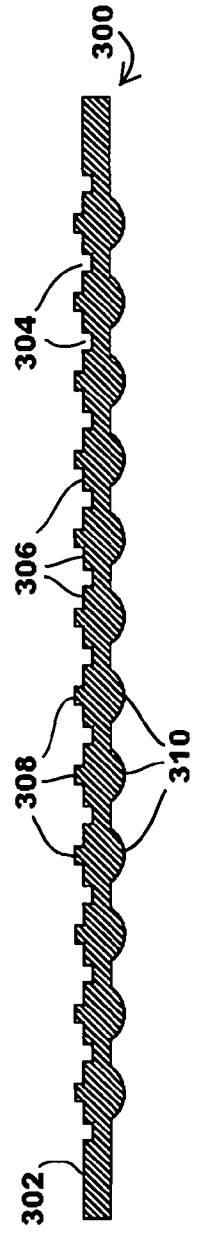
FIG. 26 is a sectional side elevation of the well plate of FIG. 24.

Referring to FIGS. 24-26 collectively, the drophead 300 has a raised outer rim 302, within which there is a reservoir 304 with 96 raised islands 306 positioned in an array within the reservoir. On each island is a raised cylindrical plinth 308 whose upper face provides a respective drop-supporting surface.

In similar manner to the single annular reservoir on drophead 22, the reservoir 304 may be filled with a liquid such as water or another solvent, and individual droplets deposited manually or using conventional robotic deposition systems on the individual drop-supporting surfaces 308, with the islands separating the reservoir from the drop-supporting surfaces. The liquid in the reservoir 304 provides an increased vapour pressure above the drophead 300 to prevent evaporation of the droplets during handling and reading. The drophead can be measured in a conventional microplate reader (not shown) by shining light through each droplet so that the liquid under test in the droplets interacts with the light and a detector or detector array under the plate detects light passing through each droplet for analysis.

As seen in FIGS. 26 and 27, a set of 96 convex lenses 310 are integrally provided on the bottom face 312 of the drophead 300, one below each island and drop-supporting surface. The lenses 310 focus the light passing through the droplet and plinth onto the detector. Alternative lens structures may be used, or they may be omitted entirely and the detector can simply collect the light passing through a flat underside of the drophead.

The invention is not limited to the embodiments described herein which may be modified without departing from the scope of the claimed invention.

What is claimed is:

1. An optical instrument comprising:
   a housing having a drop-supporting surface for receiving a droplet of liquid;
   a cover having outer and inner surfaces, the cover being mounted on the housing such that the inner surface faces the drop-supporting surface of the housing;
   a connector provided on the cover for receiving a light source and providing communication between the light source and the inner surface of the cover;
   the cover having a loading aperture extending therethrough, the aperture being spaced apart from said connector;
   a mounting provided between said cover and said housing permitting relative rotational movement between the cover and the housing about an axis between measurement and loading positions, wherein when in said measurement position the connector is positioned relative to the drop-supporting surface such that a light source received in said connector is positioned to illuminate the drop-supporting surface, and when in said loading position the loading aperture is positioned to provide access to the drop-supporting surface;
   a positioning mechanism provided between said cover and said housing to engage said cover when it reaches said measurement position and thereby ensure that the light source and drop-supporting surface are maintained in fixed spaced-apart relationship.

2. An optical instrument as claimed in claim 1, wherein said mounting further permits translational movement between the cover and the housing along said axis, and wherein the positioning mechanism is arranged to engage and hold the cover relatively closer to the housing when in said measurement position and to cause the cover to move relatively further from the housing when the cover rotates relative to the housing away from said measurement position.

3. An optical instrument as claimed in claim 2, wherein the positioning mechanism comprises means for biasing the cover towards the housing along said axis.

4. An optical instrument as claimed in claim 3, wherein the positioning mechanism further comprises complementary shaped features provided respectively on said cover and said housing, said complementary shaped features permitting the cover and housing to move closer together under the action of the biasing means when the cover is rotated relative to the housing to the measurement position, and forcing the cover and housing apart against the biasing means when the cover is rotated relative to the housing away from the measurement position.

5. An optical instrument as claimed in claim 4 wherein the complementary shaped features are a projection on one of the cover and housing and a recess on the other of the cover and housing, wherein the recess is dimensioned and positioned relative to the projection, when the cover is in the measurement position, to at least partially receive the projection, and when the cover is rotated relative to the housing away from the measurement position the projection moves out of the recess and forces the cover and housing apart.

6. An optical instrument as claimed in claim 1, wherein the housing and the cover are mutually shaped, in the vicinity of the drop-supporting-surface and the connecter respectively, to define a chamber which encloses said drop-supporting surface and with which said connector is in optical communication when the cover is in the measurement position, the chamber opening when the cover is rotated relative to the housing to the loading position to reveal the drop-supporting surface through the aperture.

7. An optical instrument as claimed in claim 6, wherein the chamber further includes a receptacle for a liquid volume, spaced apart from the drop-supporting surface.

8. An optical instrument as claimed in claim 7, wherein the receptacle for the liquid volume comprises a moat surrounding the drop-supporting surface.

9. An optical instrument as claimed in claim 6, further comprising a seal provided on one of the housing and the cover to seal said chamber and isolate it from the atmosphere.

10. An optical instrument as claimed in claim 1, wherein in addition to said loading aperture in said cover, a second loading aperture is provided in said cover, such that from the measurement position the cover may be rotated relative to the housing in one direction to reveal the drop-supporting surface through the loading aperture in said loading position and in another direction to reveal the drop-supporting surface through the second loading aperture in a second loading position.

11. An optical instrument as claimed in claim 1, further comprising a limiting mechanism provided between the housing and cover to restrict the rotation of the cover relative to the housing.

12. An optical instrument as claimed in claim 1, wherein a pair of drop supporting surfaces are provided on the housing, and said connector can be moved to a pair of measurement positions, whereby consecutive measurements may be made on samples located on each of said pair of dropheads.

13. A method of measuring an optical property of a liquid droplet, comprising the steps of:
    depositing said droplet on a drop-supporting surface through a loading aperture of an instrument cover rotationally mounted on an instrument housing, said loading aperture providing access to the drop-supporting surface when the cover is in a loading position;

rotating said cover to a measurement position wherein when in said measurement position a light source providing illumination to on an inner surface of the cover is positioned to illuminate the drop-supporting surface, and wherein when in said measurement position the light source and drop-supporting surface are maintained in fixed spaced-apart relationship.

14. Use of an optical instrument comprising the steps of:

providing an optical instrument comprising:

a housing having a drop-supporting surface for receiving a droplet of liquid;

a cover having outer and inner surfaces, the cover being mounted on the housing such that the inner surface faces the drop-supporting surface of the housing;

a connector provided on the cover for receiving a light source and providing communication between the light source and the inner surface of the cover;

the cover having a loading aperture extending therethrough, the aperture being spaced apart from said connector;

a mounting provided between said cover and said housing permitting relative rotational movement between the cover and the housing about an axis between measurement and loading positions, wherein when in said measurement position the connector is positioned relative to the drop-supporting surface such that a light source received in said connector is positioned to illuminate the drop-supporting surface, and when in said loading position the loading aperture is positioned to provide access to the drop-supporting surface;

a positioning mechanism provided between said cover and said housing to engage said cover when it reaches said measurement position and thereby ensure that the light source and drop-supporting surface are maintained in fixed spaced-apart relationship;

loading a droplet on the drop-supporting surface, rotating the cover to a measurement position, and measuring an optical property of the droplet by providing illumination from the light source to the detector, the illumination path being determined by the optical properties of the droplet.

* * * * *